US012667542B2

(12) United States Patent
Ishihara et al.

(10) Patent No.: US 12,667,542 B2
(45) Date of Patent: Jun. 30, 2026

(54) SUBSTANCE DELIVERY CARRIER AND COMPOSITION

(71) Applicants: KABUSHIKI KAISHA TOSHIBA, Tokyo (JP); The University of Tokyo, Tokyo (JP)

(72) Inventors: Mitsuko Ishihara, Setagaya (JP); Shigehisa Kawata, Niiza (JP); Susumu Goyama, Bunkyo (JP)

(73) Assignees: KABUSHIKI KAISHA TOSHIBA, Tokyo (JP); The University of Tokyo, Tokyo (JP)

( * ) Notice: Subject to any disclaimer, the term of this patent is extended or adjusted under 35 U.S.C. 154(b) by 1118 days.

(21) Appl. No.: 17/711,528

(22) Filed: Apr. 1, 2022

(65) Prior Publication Data

US 2023/0092306 A1 Mar. 23, 2023

(30) Foreign Application Priority Data

Sep. 8, 2021 (JP) ................................. 2021-146112

(51) Int. Cl.
*A61K 45/06* (2006.01)
*A61K 9/127* (2006.01)
*A61K 47/20* (2006.01)
*A61P 35/00* (2006.01)

(52) U.S. Cl.
CPC .............. *A61K 9/127* (2013.01); *A61K 45/06* (2013.01); *A61K 47/20* (2013.01); *A61P 35/00* (2018.01)

(58) Field of Classification Search
None
See application file for complete search history.

(56) References Cited

U.S. PATENT DOCUMENTS

2014/0199233 A1 7/2014 Nagy et al.
2017/0020816 A1 1/2017 Nagy et al.
2019/0247425 A1 8/2019 Sugiyama et al.
2020/0270217 A1 * 8/2020 Ishihara ............... C07D 295/15
2020/0308603 A1 10/2020 Stewart et al.
2021/0154149 A1 5/2021 Uludag et al.
2021/0246424 A1 8/2021 Akahoshi et al.

FOREIGN PATENT DOCUMENTS

JP 2010-508809 A 3/2010
JP 2013-515693 A 5/2013
JP 2014-519496 A 8/2014
JP 2020-537541 A 12/2020
JP 2021-008497 A 1/2021
JP 2021-16371 A 2/2021
JP 2021016371 * 2/2021 ......... A61K 40/4211
JP 2021016371 A * 2/2021 ......... A61K 40/4211
JP 2021-147353 A 9/2021
WO WO 2004/091572 A2 10/2004
WO WO 2011/076807 A2 6/2011
WO WO 2018/021200 A1 2/2018
WO WO 2020/039631 A1 2/2020
WO WO 2021/186233 A1 9/2021

OTHER PUBLICATIONS

Issa et al (Newcastle University PhD Thesis, Oct. 2019) (Year: 2019).*
Japanese Office Action issued Jul. 9, 2024 in Japanese Patent Application No. 2021-146112 (with unedited computer-generated English Translation), citing references 4, 15, 17-19, and 24 therein, 4 pages.
Ramishetti et al., "A Combinatorial Library of Lipid Nanoparticles for RNA Delivery to Leukocytes", Advanced Materials, vol. 32, No. 12, 2020, p. 1906128 (total 8 pages).
Martinez Soria et al., "Transient depletion of RUNX1/RUNX1T1 by RNA interference delays tumour formation in vivo", Leukemia, vol. 23, No. 1, 2009, pp. 188-190, DOI: 10.1038/leu.2008.157.
Swart et al., "Specific targeting of RUNX1/ETO; delivery of siRNA using Lipid Nanoparticles in vitro and in vivo", Klin Padiatr, vol. 232, No. 03, 2020, 1 page, DOI: 10.1055/s-0040-1709772.

* cited by examiner

*Primary Examiner* — Celeste A Roney
(74) *Attorney, Agent, or Firm* — Oblon, McClelland, Maier & Neustadt, L.L.P.

(57) ABSTRACT

According to one embodiment, a substance delivery carrier and a composition are used for delivering an intended substance to a myeloid tumor cell. The substance delivery carrier has a lipid particle, and an intended substance encapsulated in the lipid particle. The lipid particle contains, as a constituent thereof, at least a first lipid represented by formula (I).

16 Claims, 6 Drawing Sheets

Specification includes a Sequence Listing.

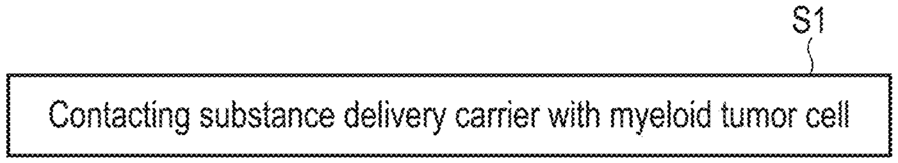
F I G. 3
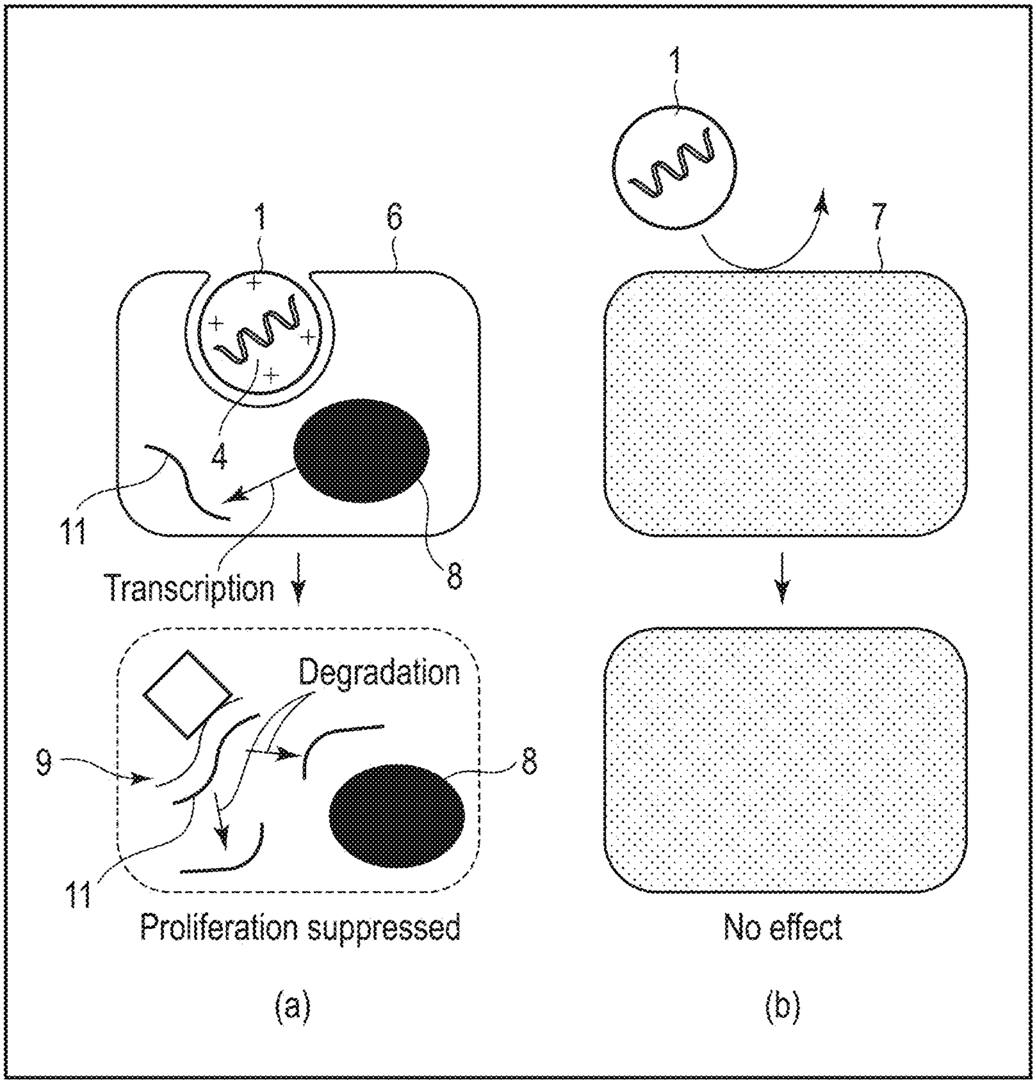
F I G. 4

SEQUENCE LISTING

<160> NUMBER OF SEQ ID NOS: 8

<210> SEQ ID NO 1
<211> LENGTH: 21
<212> TYPE: RNA
<213> ORGANISM: artificial
<220> FEATURE:
<223> OTHER INFORMATION: RUNX1_RNA

<400> SEQUENCE: 1
ccucgaagac aucggcagaa a 21

<210> SEQ ID NO 2
<211> LENGTH: 23
<212> TYPE: RNA
<213> ORGANISM: artificial
<220> FEATURE:
<223> OTHER INFORMATION: Antisense_RUNX1_RNA

<400> SEQUENCE: 2
uuucugccga ugucuucgag guu 23

<210> SEQ ID NO 3
<211> LENGTH: 20
<212> TYPE: PRT
<213> ORGANISM: artificial
<220> FEATURE:
<223> OTHER INFORMATION: Nucleic acid condensing peptide

<400> SEQUENCE: 3

```
Arg Gln Arg Gln Arg Tyr Tyr Arg Gln Arg Gln Arg Gly Gly Arg Arg
1               5                   10                  15

Arg Arg Arg Arg
            20
```

<210> SEQ ID NO 4
<211> LENGTH: 13
<212> TYPE: PRT
<213> ORGANISM: artificial
<220> FEATURE:
<223> OTHER INFORMATION: Nucleic acid condensing peptide

<400> SEQUENCE: 4

```
Arg Gln Arg Gln Arg Gly Gly Arg Arg Arg Arg Arg Arg
1               5                   10
```

<210> SEQ ID NO 5
<211> LENGTH: 21
<212> TYPE: PRT
<213> ORGANISM: artificial
<220> FEATURE:
<223> OTHER INFORMATION: Nucleic acid condensing peptide

<400> SEQUENCE: 5

```
Arg Arg Arg Arg Arg Arg Tyr Tyr Arg Gln Arg Gln Arg Gly Gly Arg
1               5                   10                  15

Arg Arg Arg Arg Arg
            20
```

<210> SEQ ID NO 6
<211> LENGTH: 39
<212> TYPE: PRT
<213> ORGANISM: artificial
<220> FEATURE:
<223> OTHER INFORMATION: Nucleic acid condensing peptide -continued

```
<400> SEQUENCE: 6

Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gly Gln Tyr Phe Ala Lys
            20                  25                  30

Pro Arg Asn Gln Gly Gly Tyr
        35


<210> SEQ ID NO 7
<211> LENGTH: 21
<212> TYPE: DNA
<213> ORGANISM: artificial
<220> FEATURE:
<223> OTHER INFORMATION: NT_RNA (combined DNA/RNA molecule)

<400> SEQUENCE: 7

auccgcgcga uaguacguat t                                              21


<210> SEQ ID NO 8
<211> LENGTH: 21
<212> TYPE: DNA
<213> ORGANISM: artificial
<220> FEATURE:
<223> OTHER INFORMATION: Antisense_NT_RNA (combined DNA/RNA molecule)

<400> SEQUENCE: 8

uacguacuau cgcgcggaut t                                              21
```

SUBSTANCE DELIVERY CARRIER AND COMPOSITION

CROSS-REFERENCE TO RELATED APPLICATIONS

This application is based upon and claims the benefit of priority from Japanese Patent Application No. 2021-146112, filed Sep. 8, 2021, the entire contents of which are incorporated herein by reference.

FIELD

Embodiments described herein relate generally to substance delivery carrier and composition.

BACKGROUND

Myeloid tumor encompassing myeloid leukemia and myeloid lymphoma is one of the malignant neoplastic disease. There has been a standing need for delivery of remedy or diagnostic drug specifically to malignant tumor cells, for the purpose of treatment and diagnosis of various malignant tumors. However, drug delivery targeted at myeloid tumor cells has encountered difficulty, and particularly nucleic acid delivery has not been successful in clinical field.

BRIEF DESCRIPTION OF THE DRAWINGS

FIG. 3 is a flow chart illustrating an exemplary substance delivery method of the second embodiment.

FIG. 4 is schematic drawing illustrating an exemplary substance delivery method of the second embodiment.

FIG. 6 is a plurality of graphs illustrating experimental results of Example 1, part (a) of wherein FIG. 6 illustrates temporal changes in the number of cells of human leukemia cell line TF-1, after introduced with lipid particles having composition B or C, encapsulating siNT or siRUNX1; part (b) of FIG. 6 illustrates temporal changes in the number of cells of human leukemia cell line Kasumi-1, after introduced with lipid particles having composition B or C and encapsulating siNT or siRUNX1; part (c) of FIG. 6 illustrates temporal changes in the number of cells of human leukemia cell line OCI-AML3, after introduced with lipid particles having composition B or C and encapsulating siNT or siRUNX1; part (d) of FIG. 6 illustrates temporal changes in the number of cells of human leukemia cell line Molm-13, after introduced with lipid particles having composition B or C and encapsulating siNT or siRUNX1.

DETAILED DESCRIPTION

Figure 1:
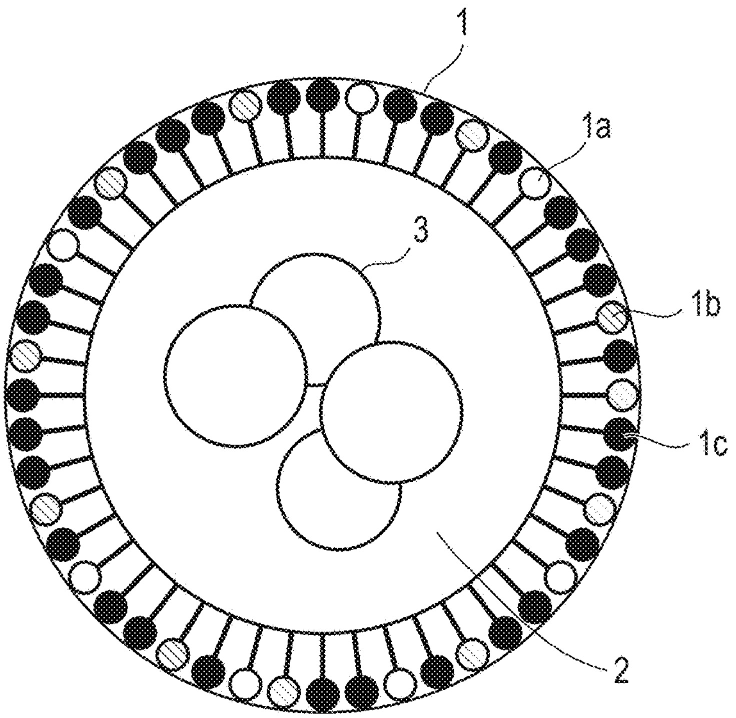
FIG. 1 is a cross sectional view illustrating an exemplary lipid particle of a first embodiment.

In general, according to one embodiment, a substance delivery carrier and a composition are used for delivering an intended substance to a myeloid tumor cell. The substance delivery carrier has a lipid particle, and an intended substance encapsulated in the lipid particle. The lipid particle contains, as a constituent thereof, at least a first lipid represented by after-mentioned formula (I).

Hereinafter, embodiments will be described with reference to the accompanying drawings. In each embodiment, substantially the same components are denoted with the same reference numerals, and descriptions thereof may be partially skipped. The drawings are only illustrative, so that relationships between thickness and planar dimension of each part, and ratios of the thicknesses of the individual parts, for example, may be different from actual ones.

First Embodiment

Lipid Particle

According to a first embodiment, there is provided a lipid particle used for introducing an intended substance into a myeloid tumor cell. As illustrated in FIG. 1, a lipid particle 1 is a near-spherical hollow article, and can encapsulate an intended substance 3 in an inner cavity 2 at the center.

The lipid particle 1 may be incorporated into the myeloid tumor cell upon contacting therewith, typically by endocytosis. The intended substance 3 can be released from the lipid particle into the cell.

Now, the myeloid tumor is a disease caused by malignant transformation of myeloid cell or lymphoid cell. The myeloid tumor cell encompasses myeloid cell that caused malignant transformation, such as myeloid cell-derived leukemia cell, lymphoma cell and so forth.

The intended substance 3 is a substance desired to be delivered into myeloid tumor cell. The intended substance 3 may only be a substance capable of being encapsulated within the lipid particle 1, and may typically be nucleic acid, protein, peptide, other organic compounds, inorganic compounds, or remedy or diagnostic drug for myeloid tumor.

The lipid particle 1 may be typically configured by a lipid membrane formed with a plurality of lipid molecules, as a material thereof, arranged with the aid of noncovalent bond. The lipid particle 1 contains, as a constituent thereof, at least a first lipid 1*a*. The first lipid 1*a* is a lipid compound represented by formula (I) below.

(I)

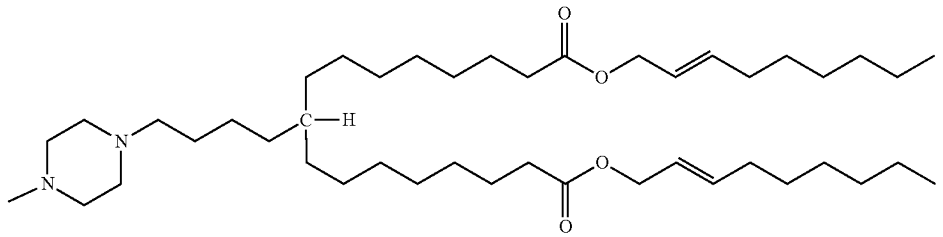

The lipid particle 1 may also contain a second lipid 1*b*, which is a lipid compound represented by formula (II) below, as a constituent thereof.

(II)

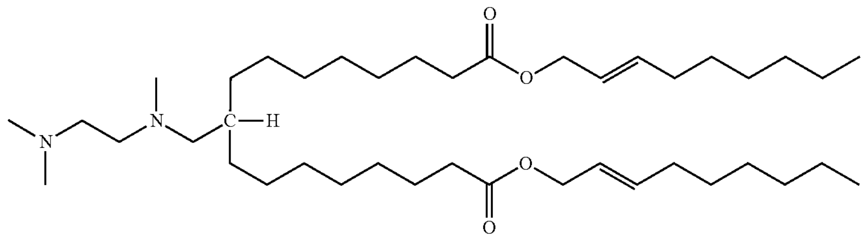

The lipid particle 1 may contain still another lipid, besides the first lipid 1*a* and the second lipid 1*b*. From among the chemical composition of lipid molecule materials composing the lipid particle 1, a composition attributable to the first lipid 1*a* will be referred to as a "first fraction", hereinafter. Meanwhile, a fraction attributable to lipid molecule materials other than the first lipid 1*a* will be referred to as a "second fraction", hereinafter. Lipids constituting in the second fraction will occasionally and collectively be referred to as a "third lipid 1*c*", hereinafter. That is, the second lipid 1*b* is one of the lipids constituting the third lipid 1*c*, and a fraction thereof constitutes the second fraction.

The terms "first fraction" and "second fraction" merely denote chemical composition of the constituents of the lipid particle 1, and by no means imply physical location of the lipids contained therein. For example, the constituents of the first fraction (the first lipid 1*a*) and that of the second fraction (the third lipid 1*c*) are not necessarily gathered independently within the lipid particle 1, instead the first lipid 1*a* and the third lipid 1*c* may exist in a mixed manner.

Ratio of blending (mole ratio) of the first lipid 1*a* relative to all lipid materials that compose the lipid particle 1 (that is, the first fraction), preferably accounts for 10% or larger and 50% or smaller for example. This case may improve introduction of the intended substance 3, in terms of specificity to myeloid tumor cell and efficiency. With the first fraction controlled to 15% or larger, the amount of introduction into living body, that is, in vivo introduction of the intended substance 3 may be improved, which is more beneficial. More preferably, the first fraction is 30% or larger. On the other hand, the upper limit of the first fraction may be 80%, 90%, 95%, 96%, 97%, 98% or 99%.

The size or permeability into the cell of lipid particle 1 may depend on the first fraction. For example, the more the first lipid 1*a*, the larger the size of lipid particle 1 may be. Average size of the lipid particle 1 may be modified depending on applications, and may be controlled typically in the range from approximately 50 nm to approximately 200 nm. When intended for use in vivo for example, the average size may occasionally be controlled within the range from approximately 50 nm to approximately 100 nm.

Type of the third lipid 1*c* is not specifically limited, and the third lipid 1*c* typically contains a base lipid. The base lipid employable here may typically be a lipid which is a major constituent of biological membrane, that is, any of phospholipid or sphingolipid, such as diacylphosphatidylcholine, diacylphosphatidylethanolamine, ceramide, sphingomyelin, dihydrosphingomyelin, cephalin or cerebroside, and combinations of them.

More specifically, for example, the base lipid employable here is preferably any of 1,2-dioleoyl-sn-glycero-3-phosphoethanolamine (DOPE), 1,2-stearoyl-sn-glycero-3-phosphoethanolamine (DSPE), 1,2-dipalmitoyl-sn-glycero-3-phosphatidylcholine (DPPC), 1-palmitoyl-2-oleoyl-sn-glycero-3-phosphatidylcholine (POPC), 1,2-di-O-octadecyl-3-trimethylammoniumpropane (DOTMA), 1,2-dioleoyl-3-dimethylammoniumpropane (DODAP), 1,2-dimyristoyl-3-dimethylammoniumpropane (14:0 DAP), 1,2-dipalmitoyl-3-dimethylammoniumpropane (16:0 DAP), 1,2-distearoyl-3-dimethylammoniumpropane (18:0 DAP), N-(4-carboxybenzyl)-N,N-dimethyl-2,3-bis(oleoyloxy)propane (DOBAQ), 1,2-dioleoyl-3-trimethylammoniumpropane (DOTAP), 1,2-dioleoyl-sn-glycero-3-phosphochlorine (DOPC), 1,2-dilinoleoyl-sn-glycero-3-phosphochlorine (DLPC), 1,2-dioleoyl-sn-glycero-3-phospho-L-serine (DOPS), or cholesterol, and combinations of any of them.

As the base lipid employable here, particularly preferred are lipids such as cationic lipid and neutral lipid, the content of which may be used for controlling acid dissociation constant of the lipid particle 1. DOTAP is preferably used as the cationic lipid, and DOPE is preferably used as the neutral lipid.

The third lipid 1*c* also preferably contains a lipid capable of preventing the lipid particle 1 from aggregating. Such anti-aggregation lipid further preferably contains polyethylene glycol (PEG)-modified lipid such as polyethylene glycol dimyristoylglycerol (DMG-PEG), polyamide oligomer derived from ω-amino(oligoethylene glycol)alkanoate monomer (U.S. Pat. No. 6,320,017 B), monosialoganglioside, or the like.

The third lipid 1*c* may additionally contain any of lipid including relatively less toxic lipid for controlling toxicity; lipid having a functional group through which a ligand is bound to the lipid particle 1; and lipid for suppressing leakage of encapsulated substance, such as sterol, and more specifically cholesterol. Cholesterol is particularly preferably contained. For example, the second fraction, when containing DOPE, DOTAP, cholesterol and PEG-modified lipid, will have excellent delivery efficiency of the intended substance 3, and is therefore preferred.

Type and chemical composition of the lipid used for the second fraction are suitably selected, considering the intended acid dissociation constant (pKa) of the lipid particle 1, particle size of the lipid particle 1, type of the intended substance 3, stability of the lipid particle 1 in the cell, and so forth.

As illustrated in FIG. 4, the lipid particle 1, which is weakly cationic, is likely to be incorporated into the myeloid tumor cell, but unlikely to be incorporated into other cell 7 such as normal myeloid cell. More specifically, the lipid composition of the lipid particle 1 is preferably configured so that the lipid particle 1 will have an acid dissociation constant (pKa) of 8.4 or smaller, for example. The acid dissociation constant (pKa) of lipid particle varies with a peripheral ionic strength (I). The ionic strength (I) is calculated by equation (1) below. The acid dissociation constant (pKa) in the present specification is specified as a value demonstrated in an environment with an ionic strength (I) of $3.599\times10^{-3}$ mol/dm$^3$.

$$I = \frac{1}{2}\sum_i x_i z_i^2 \qquad \text{Equation (1)}$$

In equation (1), $m_i$ represents molar concentration of each ion existing around lipid particles, and $z_i$ represents charge amount of each ion.

An acid dissociation constant (pKa) of 8.4 or smaller may be achieved, if the content of cationic lipid in the lipid composition of the lipid particle 1 is set larger than the content of anionic lipid. Examples of the composition (mole ratio) of the lipid particle that can demonstrate the acid dissociation constant of a pKa of 8.4 or smaller includes a composition given by first lipid 1*a*:DOPE:DOTAP:cholesterol:PEG=31.7:4.5:9.0:51.4:3.4 (the lipid particle in this case will have a pKa of 8.1); and a composition given by second lipid 1*b*:first lipid 1*a*:DOPE:DOTAP:cholesterol:PEG=15.0:30.1:9.0:4.0:37.9:4.0 (the lipid particle in this case will have a pKa of 7.6). Now the cationic lipid refers to a lipid having a positively charged group. In the lipid composition above, the first lipid 1*a*, the second lipid 1*b*, and DOTAP correspond to the cationic lipid.

By a simple procedure such as encapsulating the intended substance 3 into the lipid particle 1, and by contacting (administering, for example) it with myeloid tumor cell, it now becomes possible to efficiently introduce the intended substance 3 into the myeloid tumor cell, without using an antigen or receptor having been used in the prior method. The lipid particle 1 can therefore be used for various applications where the intended substance 3 is necessarily delivered selectively or specifically to the myeloid tumor cell.

The lipid particle 1 may optionally encapsulate an additional ingredient, besides the intended substance 3. The additional ingredient is typically pH adjustor, osmoregulator, or any of other remedies or diagnostic drugs for myeloid tumor cell. The pH adjustor is typically organic acid such as citric acid, or salt thereof. The osmoregulator is typically sugar or amino acid. The lipid particle 1 that encapsulates the intended substance 3 and other optional substance may be manufactured, typically by any of known methods for encapsulating small molecules into lipid particle, such as the Bangham method, organic solvent extraction method, surfactant removal method, and freeze-thaw method. For example, prepared are a lipid mixture obtained by adding materials of the lipid particle 1 according to a desired ratio into an organic solvent such as alcohol, and an aqueous buffer that contains an ingredient to be encapsulated such as the intended substance 3, and the aqueous buffer is then poured into the lipid mixture. The obtained mixture is stirred and thus suspended, thereby forming the lipid particle 1 in which the intended substance 3 and so forth are encapsulated.

Ratio of blending of the constituents of the lipid particle 1 is easily controllable by changing the ratio of blending of the individual materials in the lipid mixture. For example, the ratio of mixing of the constituents of the lipid particle 1 may be nearly equal to the ratio of mixing of the individual materials in the lipid mixture. Ratio of amounts of the substances to be encapsulated in the lipid particle 1 is easily controllable by changing the ratio of amounts of the individual substances in the aqueous buffer.

The lipid particle 1 having the intended substance 3 encapsulated therein will also be referred to as "substance delivery carrier", hereinafter.

Composition

The substance delivery carrier may also be provided in the form of liquid composition impregnated in a proper carrier. The carrier may typically be water, aqueous sodium chloride solution such as saline, aqueous glycine solution, buffer, or the like. The substance delivery carrier may alternatively be provided in the form of dry powdery composition. The powdery composition will be made usable by the user adding a proper liquid such as the aforementioned carrier.

The composition may further contain a substance that improves storage stability (that is, storage protectant), besides the substance delivery carrier. The storage protectant is exemplified by, but not specifically limited to, albumin, lipoprotein, apolipoprotein, glycoprotein such as globulin; pH adjustor, buffering agent, tonicity adjustor, etc.; pharmaceutically acceptable participant capable of assimilating the composition to the physiological state, such as sodium acetate, sodium lactate, sodium chloride, potassium chloride and calcium chloride; lipophilic free radical quencher such as α-tocopherol, capable of suppressing damage induced by free radical; lipid protective agent such as water-soluble chelator represented by ferrioxamine, capable of suppressing peroxidative damage of lipid and of improving storage stability; freeze protectant for example glycerin, dimethylsulfoxide and sugars such as sucrose and trehalose.

When using the substance delivery carrier for administration to living body, the composition preferably has a pharmaceutically acceptable chemical composition, and is sterilized by any of known methods.

Second Embodiment

In a second embodiment, an exemplary usage of the lipid particle 1 for reducing or extinguishing the myeloid tumor cell will be explained. In this case, a substance for suppressing proliferation of the myeloid tumor cell is employable as the intended substance 3.

The lipid particle 1 that encapsulates such intended substance 3, that is, an exemplary substance delivery carrier 10, will be explained referring to FIG. 2.

Substance Delivery Carrier

Figure 2:
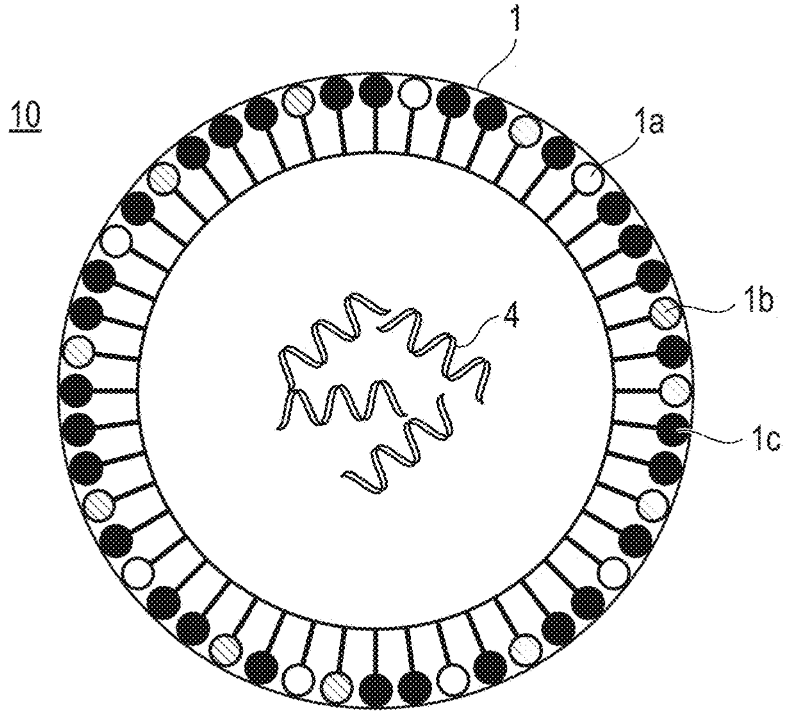
FIG. 2 is a cross sectional view illustrating an exemplary substance delivery carrier of a second embodiment.

As illustrated in FIG. 2, the substance delivery carrier 10 has a lipid particle 1, and RNA 4 encapsulated in the lipid particle 1.

The lipid particle 1 employable here may be any of the lipid particles 1 explained in the first embodiment.

The RNA 4 acts to suppress expression of a gene relevant to onset and progression of myeloid tumor cell. Expression of the gene relevant to onset and progression of myeloid tumor cells can be suppressed, typically by destroying a transcript of the gene. The transcript is, for example, messenger RNA (mRNA). The RNA 4 may typically be siRNA (small interfering RNA) that demonstrates an action of decomposing mRNA with the aid of RNA interference. The mRNA to be decomposed by siRNA may either be Pre-mRNA before being spliced, or matured mRNA after being spliced. The RNA 4 may alternatively be siRNA that includes a sense strand having a sequence complementary to a part of gene sequence relevant to onset and progression of myeloid tumor cell, and an antisense strand thereof.

The gene relevant to onset and progression of myeloid tumor cell is exemplified by transcription factors (RUNX1, RUNX2, MECOM, MYB, MYC, HOXA9, MEIS1, HHEX, and ERG), fusion genes (RUNX1-RUNX1T1, KMT2A-AFF1, KMT2A-MLLT1, KMT2A-MLLT3, BCR-ABL), epigenome control factors (EZH2, EED, BAP1, KDM1A, RCOR1, SETDB1, TRIM33, JARID2, CARM1, SETD1B, BRD2, BRD4, PRMT1, PRMT4, PRMT5, DOT1L, CARM1, NSD1), phosphorylating enzymes (CDK9, AXL), immunosuppressive factors (CD274, CD38, CD47, CD155, CD112), ubiquitin-related factors (FBXW7, UBE2E1), apoptosis control factors (BCL2, MCL1, BCL2L1), and non-coding RNAs (NEAT1, MALAT1, HOTAIR, miR-125). RUNX1, RUNX2, MECOM, MYB, MYC, HOXA9, MEIS1, HHEX, and ERG are particularly desirable.

The RNA 4 according to the embodiment may typically be siRNA that includes RUNX1 RNA (see SEQ ID NO: 1, Table 1) having a sequence complementary to a part of the sequence of transcription factor RUNX1, and antisense RUNX1 RNA (see SEQ ID NO: 2, Table 1).

TABLE 1

| SEQ ID NO | SEQ Name | Base sequence |
|---|---|---|
| 1 | RUNX-1_RNA | 5'-CCUCGAAGACAUCGGCAGAAA-3' |
| 2 | Antisense_RUNX-1_RNA | 3'-UUGGAGCUUCUGUAGCCGUCUUU-5' |

The RNA 4 according to the embodiment may alternatively be, for example, siRNA having a sequence complementary to a part of the sequence of the fusion gene RUNX1-RUNX1T1.

The RNA 4 may alternatively contain an additional sequence in addition to the sequence of siRNA that suppresses expression of a gene relevant to onset and progression of myeloid tumor cell. The additional sequence may typically be an overhang sequence.

The RNA 4 may alternatively be a modified RNA which may typically be intended for imparting decomposition resistance. Such modification may only be any of known modifications that make the RNA insusceptible to decomposition typically with RNase, and the modification is exemplified by use or introduction of a naturally occurring modification nucleotide or a non-naturally occurring nucleotide into the RNA, or, use or addition of a non-naturally occurring sequence to the RNA.

The naturally occurring modification nucleotide is exemplified by pseudouridine, 5-methylcytidine, and 1-methyladenosine. The non-naturally occurring nucleotide is exemplified by BNA (bridged nucleic acid), LNA (locked nucleic acid), and PNA (peptide nucleic acid).

The non-naturally occurring sequence is typically an artificially produced base sequence that does not occur naturally, and may contain a mismatched base in a part of the sequence.

Increased amount of administration of the RNA 4 may more largely suppress expression of the gene relevant to onset and progression of myeloid tumor cells. Hence, the lipid particle 1 preferably contains an increased amount of RNA 4. For example, the lipid particle 1 preferably contains approximately 2000 more copies of RNA. The amount of encapsulation of the RNA 4 depends on three-dimensional structure and base sequence length of the RNA 4, and lipid composition of the lipid particle 1.

The RNA 4 may be encapsulated in its intact form in the lipid particle 1, or after condensed with a nucleic acid condensing peptide. Use of the nucleic acid condensing peptide can condense the nucleic acid in a compact size, enabling the lipid particle 1 to contain a large amount of the RNA 4 while keeping the size small. This also reduces the amount of the RNA 4 that remains outside the lipid particle 1, thereby preventing aggregation of the substance delivery carriers 10. Efficiency of delivery of the RNA 4 may thus be enhanced.

A preferred nucleic acid condensing peptide is a peptide that contains cationic amino acid which accounts for 45% or more of the whole. More preferred nucleic acid condensing peptide has sequence RRRRRR (first amino acid sequence) at one terminal, and has sequence RQRQR (second amino acid sequence) at the other terminal. Between the first amino acid sequence and the second amino acid sequence, there is no, or one or more intermediate sequences of RRRRRR or RQRQR. There are two or more neutral amino acids interposed between any of two adjacent sequences from among the first amino acid sequence, the second amino acid sequence, and the intermediate sequence. The neutral amino acid is typically G or Y. The other terminal may alternatively have RRRRRR (first amino acid sequence), in place of the second amino acid sequence.

The nucleic acid condensing peptide preferably has amino acid sequences below.

(SEQ ID NO: 3)
RQRQRYYRQRQRGGRRRRRR (SEQ ID NO: 4)
RQRQRGGRRRRRR (SEQ ID NO: 5)
RRRRRRYYRQRQRGGRRRRRR.

Again alternatively, a nucleic acid condensing peptide having an amino acid sequence below may be used in combination with any of the aforementioned nucleic acid condensing peptide.

(M9)
(SEQ ID NO: 6)
GNQSSNFGPMKGGNFGGRSSGPYGGGGQYFAKPRNQGGY

This peptide can further condense the nucleic acid aggregate having been condensed with the aforementioned nucleic acid condensing peptide.

The RNA 4 may be condensed typically by mixing the RNA 4 with the nucleic acid condensing peptide under stirring, before being encapsulated into the lipid particle 1.

The lipid particle 1 may optionally encapsulate therein pH adjustor, osmoregulator, or other remedy for myeloid tumor cell and so forth, besides the RNA 4.

Substance Delivery Method

The paragraphs below will explain a substance delivery method for suppressing proliferation of the myeloid tumor cell, by delivering RNA that suppresses expression of a gene relevant to onset and progression of the myeloid tumor cell to the myeloid tumor cells, with use of a substance delivery carrier 10 of the second embodiment. The substance delivery method of the second embodiment includes, as illustrated in FIG. 3, contacting the substance delivery carrier 10 of the embodiment, with the myeloid tumor cell (contact step S1).

The myeloid tumor cell typically exists in vivo in a subject. The subject is preferably human, but may be any of animals other than human. The animals are preferably mammals. The subject may be the one having already been diagnosed to have myeloid tumor, or may be the one having been suffered from, or suspected of having myeloid tumor.

The contact step S1 in this case is carried out by administering the composition that contains the substance delivery carrier 10 to the subject. Route of administration is not specifically limited, and may be any of intravenous injection, subcutaneous injection, intramuscular injection, arterial injection, epidural injection, cerebrospinal cavity injection, intrathoracic injection, intraperitoneal injection, local intralesional injection, or systemic administration typically by intravenous drip. Administration schedule may only be selectable, typically considering application; and sex, age, body weight and pathological condition of the subject, and may be single administration, or may be repetitive or periodical multiple administration. Upon being administered, the substance delivery carrier 10 is conveyed typically by blood, and brought into contact in vivo with the myeloid tumor cell 6.

As illustrated in part (a) of FIG. 4, the substance delivery carrier 10, brought into contact with the myeloid tumor cell 6, is then incorporated into the myeloid tumor cell 6 typically by endocytosis. The RNA 4 is thus introduced into the myeloid tumor cell 6, and the RNA 4 then suppresses expression of a gene 8 relevant to onset and progression of the myeloid tumor cell, in the myeloid tumor cells 6. If the RNA 4 is siRNA, the siRNA after being introduced into the cell is dissociated into a single strand, and an argonaute then binds to the antisense strand, to form an RNA-induced silencing complex (RISC) 9 which is a nucleic acid-protein complex. The RISC 9 specifically binds for example to mRNA 11, which is a transcript of the gene relevant to onset and progression of the myeloid tumor cell, and cleaves the binding site, to thereby decompose the mRNA 11. Such suppression of gene expression in this manner can suppress proliferation of the myeloid tumor cell 6 in the subject.

Known methods for introducing siRNA into a cell include a method by which a DNA (shRNA) that encodes siRNA is introduced into a genome of a target cell typically with use of a lentiviral vector, and the genome is allowed to express to cause intracellular production of siRNA; and a method by which shRNA is introduced into a cell typically with use of a vector such as a plasmid, and shRNA is transcribed to produce siRNA. These known methods have, however, suffered from technical problems that the amount of expression is limitative, since only several tens at the largest of copies of the siRNA can be introduced per cell; that a certain period is necessary before the expression, thus limiting quick-acting property of a remedy; and that safety has to be ensured since the genome of a host cell is modified.

The substance delivery carrier 10 according to the embodiment introduces RNA in the form of siRNA, and does not require gene expression in the cell of the subject. The antiproliferative effect against the myeloid tumor cell may therefore be exerted immediately on the subject, while limiting any influence of the substance delivery carrier 10 on the subject within a transient level. That is, use of the substance delivery carrier 10 according to the embodiment can shorten a period of treatment than in any of known methods, can relieve a burden on the subject as compared with any of known methods, and is thus preferred for its excellence in safety.

The substance delivery carrier 10 according to the embodiment can encapsulate approximately 1000 copies of siRNA. The substance delivery carrier 10 according to the embodiment can therefore introduce a larger amount of copies of siRNA into a myeloid tumor cell, than by any of the known methods. The substance delivery carrier 10 according to the present embodiment therefore demonstrates an improved therapeutic effect on myeloid tumor.

EXAMPLES

Exemplary manufacture and usage of the substance delivery carrier of the embodiment will be explained below.

Example 1: Evaluation of Amount of Introduction of Lipid Particles into Myeloid Tumor Preparation of Substance Delivery Carrier A plurality of types of siRNA to be encapsulated in a lipid particle, and lipid solutions in ethanol were prepared. Base sequences of siRNA to be encapsulated are summarized in Table 2, and compositions of the lipid solutions in ethanol are summarized in Table 3.

TABLE 2

| SEQ ID NO | SEQ Name | Base sequence |
|---|---|---|
| 1 | RUNX-1_RNA | 5'-CCUCGAAGACAUCGGCAGAAA-3' |
| 2 | Antisense_RUNX-1_RNA | 3'-UUGGAGCUUCUGUAGCCGUCUUU-5' |
| 7 | NT_RNA | 5'-AUCCGCGCGAUAGUACGUATT-5' |
| 8 | Antisense_NT_RNA | 3'-TTUAGGCGCGCUAUCAUGCAU-5' |

siRNAs to be encapsulated in the lipid particle were double-stranded RNAs, which were siRNA in which a part of RUNX1 RNA (SEQ ID NO: 1) and a part of antisense RUNX1 RNA (SEQ ID NO: 6) are complementarily bound (referred to as siRUNX1, hereinafter); and siRNA in which a part of NT RNA (SEQ ID NO: 7) and a part of antisense NT RNA (SEQ ID NO: 8) are complementarily bound (referred to as siNT, hereinafter).

siRUNX1 is a kind of siRNA capable of acting to decompose and destroy mRNA which is a transcript of a gene relevant to onset and progression of the myeloid tumor cell. On the other hand, siNT is a kind of siRNA having a base sequence whose length (approximately 20 bp) is nearly equal to that of siRUNX1, but does not act to decompose or destroy such mRNA. Therefore, an effect proving that the intended substance is siRUNX1 may be clarified by using a lipid particle that encapsulates siNT as a control, and by subjecting the control to an experiment in the same way as a lipid particle that encapsulates siRUNX1 is tested.

TABLE 3

| Composition | FFT-20 | FFT-10 | DOPE | DOTAP | Chol | PEG |
|---|---|---|---|---|---|---|
| A | 0.0 | 39.0 | 6.0 | 22.0 | 31.0 | 2.0 |
| B | 31.7 | 0.0 | 4.5 | 9.0 | 51.4 | 3.4 |
| C | 30.1 | 15.0 | 9.0 | 4.0 | 37.9 | 4.0 |

Table 3 summarizes compositions A, B, and C (mole ratio) of three types of lipid solution in ethanol used in this example. As described previously, since the ratio of mixing of the constituents of the lipid particle 1 is nearly same as the ratio of mixing of the individual materials in the lipid mixture, the compositions A, B, and C represent compositions in mole ratio of the individual lipid particles prepared by using the lipid solutions in ethanol. "FFT-20" corresponds to a compound represented by formula (I), and "FFT-10" corresponds to a compound represented by formula (II). "Chol" in Table 3 represents cholesterol.

(I)

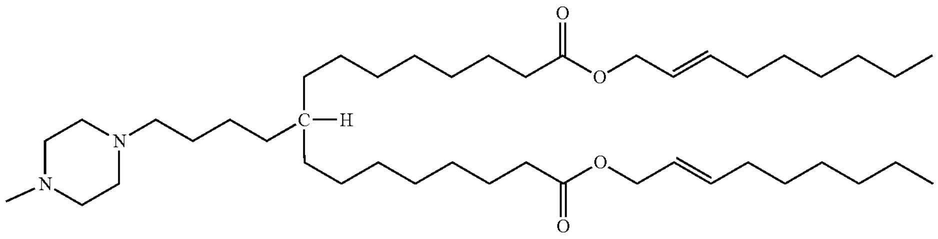

(II)

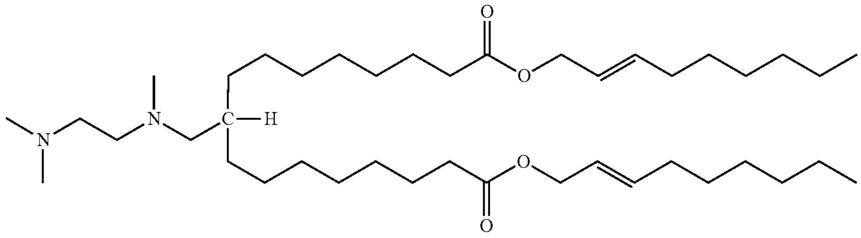

To the lipid solution in ethanol listed in in Table 3, 10 mM HEPES (pH 7.3) having siRNA listed in Table 2 dissolved therein was added, and the mixture was suspended by pipetting. To the solution, added was 7 times as much of a 10 mM HEPES buffer (pH 7.3), and the solution was then condensed and replaced with the 10 mM HEPES buffer (pH 7.3) with use of an ultrafiltration device (Amicon Ultra-0.5 mL, Ultracel-50 K, from Millipore), to thereby obtain each lipid particle that encapsulates siRNA. Total amount of RNA encapsulated in the lipid particle was measured with use of an RNA quantitation kit QuantiFluor (Registered trademark) RNA System (from Promega Corporation). Total number of lipid particles was measured by using a particle characterization apparatus “NanoSight” (from Malvern Panalytical Ltd.). Amount of RNA contained in a lipid particle was calculated by dividing the measured total amount of RNA by the total number of lipid particles.

Results

Table 4 summarizes the number of copies of RNA encapsulated in the lipid particles with composition A and B.

TABLE 4

| Composition | Type of nucleic acid | Amount of encapsulated nucleic acid (μg/ml) | Number of copies of encapsulated nucleic acid (/lipid particle) |
|---|---|---|---|
| A | siRNA (approx. 20 bp) | 200 | $0.8 \times 10^3$ |
| B | siRNA (approx. 20 bp) | 500 | $2.0 \times 10^3$ |

Referring to the results in Table 4, the amount of nucleic acid encapsulated in the lipid particle with composition B was found to be larger than the amount of nucleic acid encapsulated in the lipid particle with composition A, proving that the lipid particle with composition B can encapsulate a larger amount of nucleic acid. This result indicates that the chemical composition of the lipid particle affects the number of copies of nucleic acid that can be encapsulated, and that the lipid composition of the lipid particle is preferably set equal to or closer to composition B, in order to increase the amount or concentration of nucleic acid to be encapsulated.

Measurement of Acid Dissociation Constant (pKa) of Lipid Particle

Each of the lipid particles with the lipid compositions summarized in Table 3, which amounts 0.1 μg, was diluted with 10 mL of a 10 mM HEPES buffer (pH 7.3). The HEPES buffer that contains each lipid particle was placed in a measurement cell of a dynamic light scattering measuring instrument “Zetasizer Nano ZSP” (from Malvern Panalytical Ltd.), and titrated with use of 0.25 M hydrochloric acid and a 0.25 M aqueous sodium hydroxide solution, within the pH range from 5.0 to 11.0. The acid dissociation constant was calculated from result of the titration. Since the acid dissociation constant is unique to each substance and varies depending on ionic strength, so that the ionic strength (I) of the 10 mM HEPES-Na buffer (pH 7.3) used in this experiment was theoretically calculated to be $I=3.599\times10^{-3}$ mol/$dm^3$.

Results

Table 5 summarizes the acid dissociation constants of the individual lipid particles with lipid composition A, B, or C.

TABLE 5

| Composition No. | pKa |
|---|---|
| A | 8.5 |
| B | 8.1 |
| C | 7.6 |

Referring to the results in Table 5, the acid dissociation constants of the lipid particles with composition B and composition C are smaller than the acid dissociation constant of the lipid particle with composition A. This result suggests that the chemical composition of lipid particle affects the acid dissociation constant of the lipid particle. That is, it is understood that the lipid composition of the lipid particle is preferably set closer to composition B or C, rather than to composition A, for the purpose of further lowering the acid dissociation constant of the lipid particle. The phrase set closer to composition B or C, rather than to composition A" means that, if there is any numerical range that is not satisfied by composition A but commonly satisfied by compositions B and C, the lipid composition is set within such numerical range. More specifically, the lipid composition of the lipid particle preferably contains at least FFT-20. The lipid composition of the lipid particle is more preferable if the percentage (mole ratio) of EFT-20 is approximately 30% or larger.

Preparation of Myeloid Tumor Cells

Various human leukemia cell lines were prepared as the myeloid tumor cells. More specifically, TF-1 (derived from erythroleukemia), Kasumi-1 (derived from acute myeloblastic leukemia), OCI-AML3 (derived from acute myelogenous leukemia), and Molm-13 (derived from acute myelogenous leukemia) were prepared. These cells were prepared on a 24-well culture, while seeded at a concentration of $1\times10^5$/1000 μl.

Introduction of Lipid Particles into Myeloid Tumor Cells

On the plate seeded with the individual myeloid tumor cells, 1 μg of lipid particle was added, the content was thoroughly mixed by pipetting, and then cultured in an incubator conditioned at 37° C. and with an atmosphere of 5% $CO_2$. The cells were collected from the culture plate every two days for counting of the number of cells, and one-fifth of the cells were re-seeded on the 24-well culture plate every time the collection and measurement take place, and 1 μg of lipid particles were added thereto to restart the culture. On day 8 from the start of culture, the cells were collected, treated with a lysis buffer, separated by gel electrophoresis, and subjected to Western blotting. Anti-RUNX1 antibody was used for staining.

Results

Figure 5:
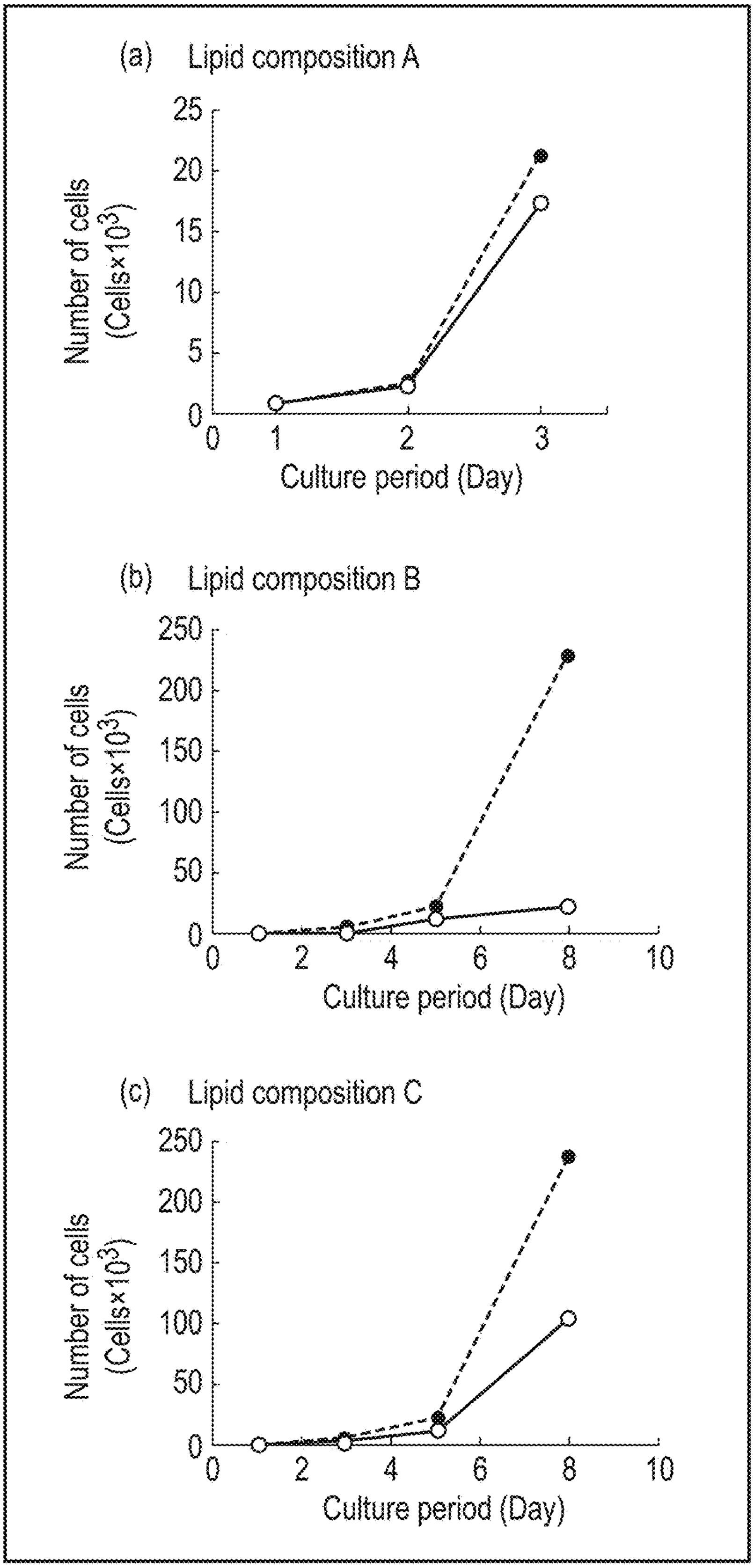
FIG. 5 is a plurality of graphs illustrating experimental results of Example 1, wherein part (a) of FIG. 5 illustrates temporal changes in the number of cells of human leukemia cell line TF-1, after introduced with lipid particles having composition A and encapsulating siNT or siRUNX1; part (b) of FIG. 5 illustrates temporal changes in the number of cells of human leukemia cell line TF-1, after introduced with lipid particles having composition B and encapsulating siNT or siRUNX1; part (c) of FIG. 5 illustrates temporal changes in the number of cells of human leukemia cell line TF-1, after introduced with lipid particles having composition C and encapsulating siNT or siRUNX1.

Part (a) of FIG. 5 illustrates temporal changes in the number of cells of human leukemia cell line TF-1, after introduced with the lipid particles having composition A and encapsulating siNT or siRUNX1. Part (b) of FIG. 5 illustrates temporal changes in the number of cells of human leukemia cell line TF-1, after introduced with the lipid particles having composition B and encapsulating siNT or siRUNX1. Part (c) of FIG. 5 illustrates temporal changes in the number of cells of human leukemia cell line TF-1, after introduced with the lipid particles having composition C and encapsulating siNT or siRUNX1. In FIG. 5, the broken line indicates that the encapsulated siRNA is siNT, and the solid line indicates that the encapsulated siRNA is siRUNX1.

Referring now to part (a) of FIG. 5, the number of the myeloid tumor cells having the lipid particles with lipid composition A introduced therein was found to increase almost similarly in both cases where siNT and siRUNX1 were used, with a slight suppressive effect on proliferation demonstrated by siRUNX1. Referring to Part (a) and (b) of FIG. 5, the myeloid tumor cells, to which the lipid particles with lipid composition B or C and having siRUNX1 encapsulated therein was introduced, was found to be suppressed in proliferation. In particular, a remarkable suppressive effect on proliferation was demonstrated, in a case where the lipid particle encapsulating siRUNX1 has lipid composition B.

It is therefore understood that the suppressive effect on cell proliferation, demonstrated by the lipid particle that encapsulate siRUNX1, is affected by the lipid composition of the lipid particle, which was more remarkable in the cases with compositions B and C, than in the case with composition A. This is presumably because the lipid composition of the lipid particle affects the number of copies of nucleic acid that can be encapsulated and the acid dissociation constant of the lipid particle, as described above.

Figure 6:
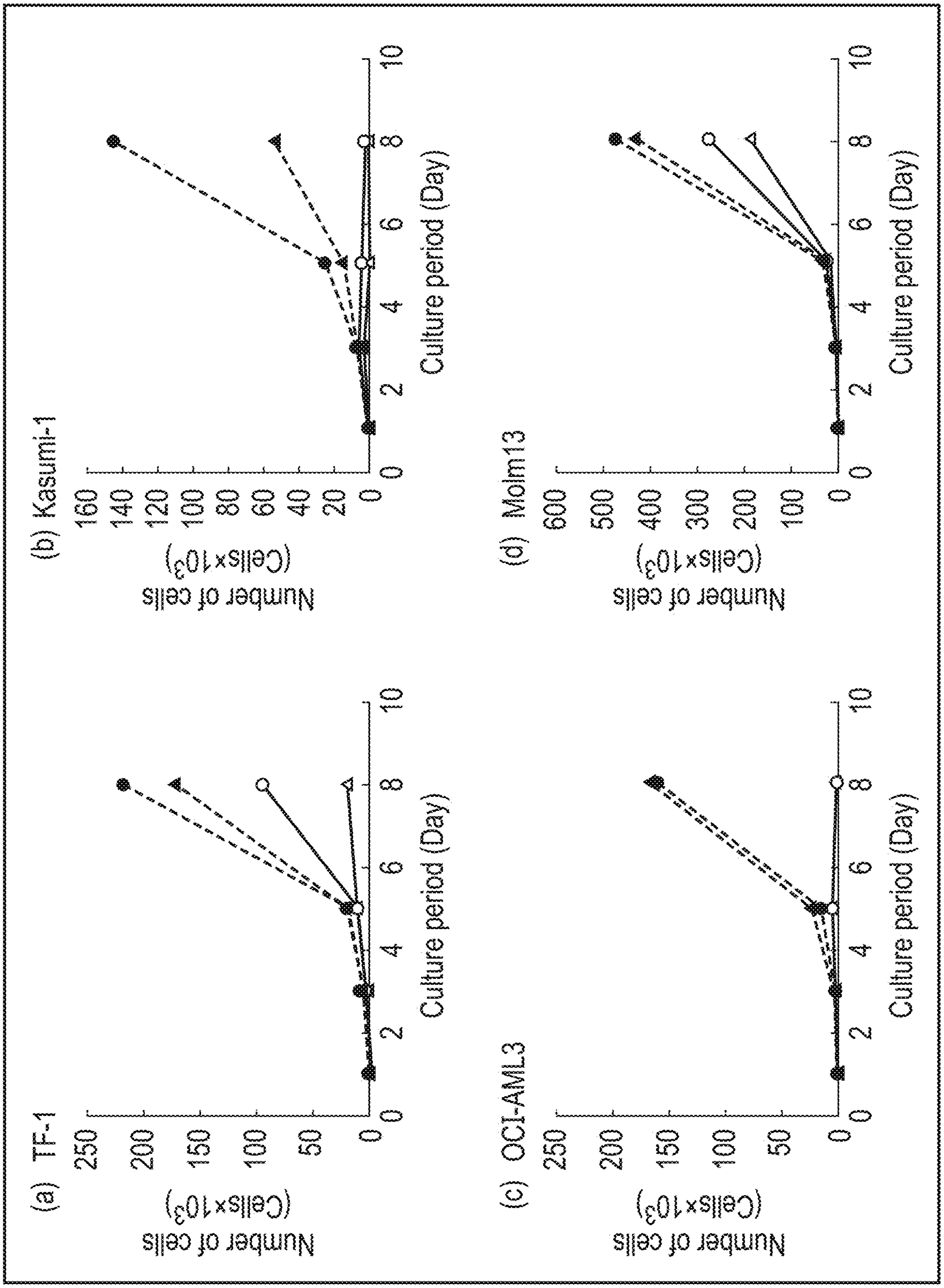

Part (a) of FIG. 6 illustrates temporal changes in the number of cells of human leukemia cell line TF-1, after introduced with the lipid particles with composition B or C, encapsulating siNT or siRUNX1. Part (b) of FIG. 6 illustrates temporal changes in the number of cells of human leukemia cell line Kasumi-1, after introduced with the lipid particles having composition B or C and encapsulating siNT or siRUNX1. Part (c) of FIG. 6 illustrates temporal changes in the number of cells of human leukemia cell line OCI-AML3, after introduced with the lipid particles having composition B or C and encapsulating siNT or siRUNX1. Part (d) of FIG. 6 illustrates temporal changes in the number of cells of human leukemia cell line Molm-13, after introduced with the lipid particles having composition B or C and encapsulating siNT or siRUNX1. In FIG. 6, the ordinate plots the number of cells (Cells$\times 10^3$), and the abscissa plots the culture period (Days). In FIG. 6, triangle plots indicate temporal changes in the number of cells having introduced therein the lipid particle with composition B; circle plots indicate temporal changes in the number of cells having introduced therein the lipid particle with composition C; broken line indicates that the encapsulated siRNA is siNT; and the solid line indicates that the encapsulated siRNA is siRUNX1.

Referring to Part (a), (b), (c) and (d) of FIG. 6, all cases with the human leukemia cell lines TF-1, Kasumi-1, COI-AML3, and Molm-13 were found to increase the number of cells after introduced with the lipid particles having composition B or C and encapsulating siNT; meanwhile found to demonstrate the suppressive effect on cell proliferation after introduced with the lipid particles with composition B or C and encapsulating siRUNX1. Hence, the lipid particles having lipid composition B or C and encapsulating siRUNX1 were proved to demonstrate the suppressive effect on the myeloid tumor cells, regardless of the type of myeloid tumor cells.

Figure 7:
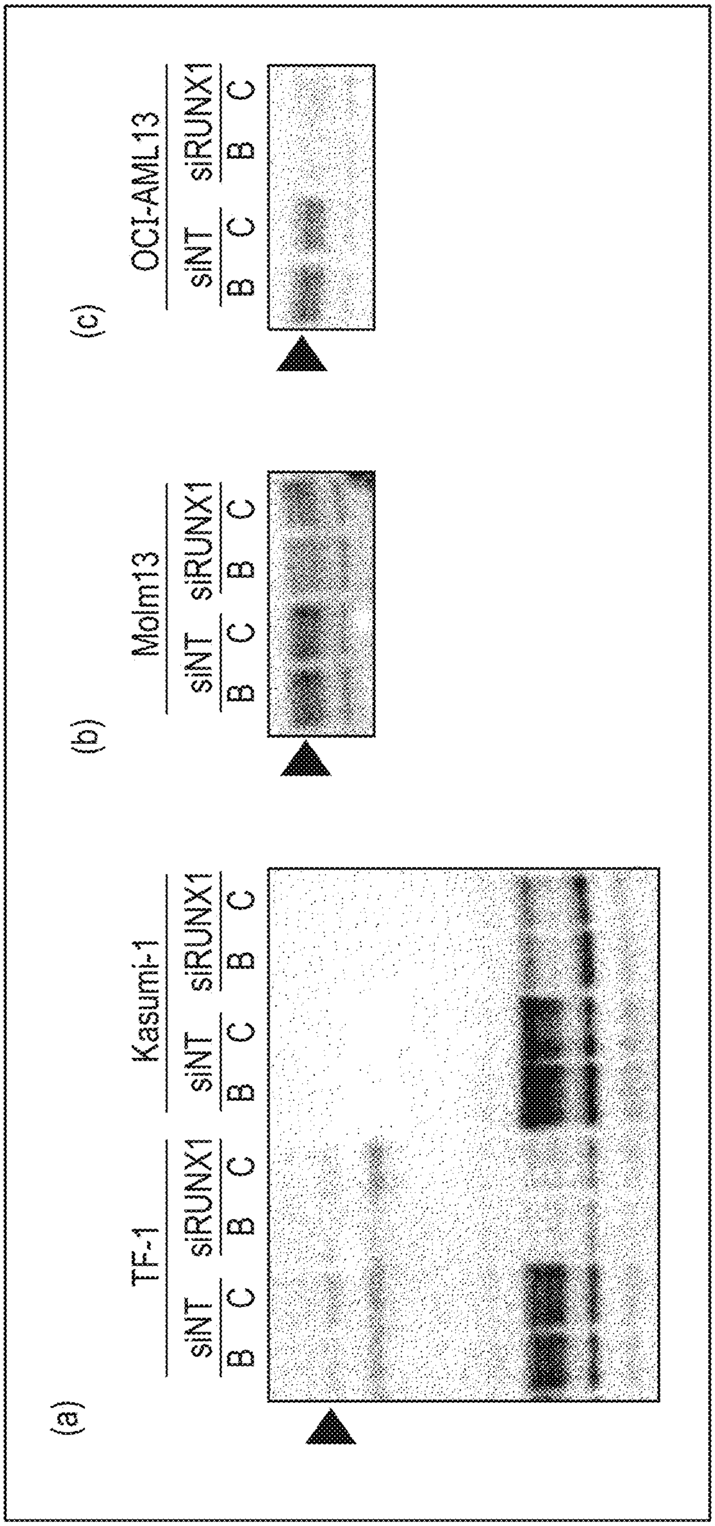
FIG. 7 is a plurality of photographs illustrating experimental results of Example 1, wherein part (a) of FIG. 7 illustrates analytical results of proteins extracted from cells of human leukemia cell line TF-1 or Kasumi-1, after introduced with lipid particles that encapsulate siNT or siRUNX1; part (b) of FIG. 7 illustrates analytical results of proteins extracted from a cell of human leukemia cell line OCI-AML3, after introduced with lipid particles that encapsulate siNT or siRUNX1; part (c) of FIG. 7 illustrates analytical results of proteins extracted from a cell of human leukemia cell line Molm-13, after introduced with lipid particles that encapsulate siNT or siRUNX1.

Part (a) of FIG. 7 illustrates analytical results of proteins extracted from cells of human leukemia cell line TF-1 or Kasumi-1, after introduced with the lipid particles that encapsulate siNT or siRUNX1. Part (b) of FIG. 7 illustrates analytical results of proteins extracted from a cell of human leukemia cell line OCI-AML3, after introduced with the lipid particles that encapsulate siNT or siRUNX1. Part (c) of FIG. 7 illustrates analytical results of proteins extracted from a cell of human leukemia cell line Molm-13, after introduced with the lipid particles that encapsulate siNT or siRUNX1.

Referring to FIG. 7, abundance of a band attributable to RUNX1 protein, indicated by a right-pointing triangle, was found to decrease in all cell groups administered with the lipid particles with composition B or C, encapsulating siRUNX1. Hence, introduction of the lipid particles with lipid composition B or C and encapsulating siRUNX1 was proved to suppress expression of RUNX1 protein, regardless of the types of myeloid tumor cell.

Example 2: Evaluation of Amount of Introduction of Lipid Particles into Cell Derived from Patient with Myelogenous Leukemia Preparation of Cell Derived from Patient with Myelogenous Leukemia, and Introduction of Lipid Particles PDX-AML-1, which is a cell derived from a patient with myelogenous leukemia, was prepared. The lipid particles were introduced in the same way as the introduction into the myeloid tumor cells described above, and also the temporal changes in the number of cells during culture was measured in the same way as the measurement of the myeloid tumor cells.

Results

Figure 8:
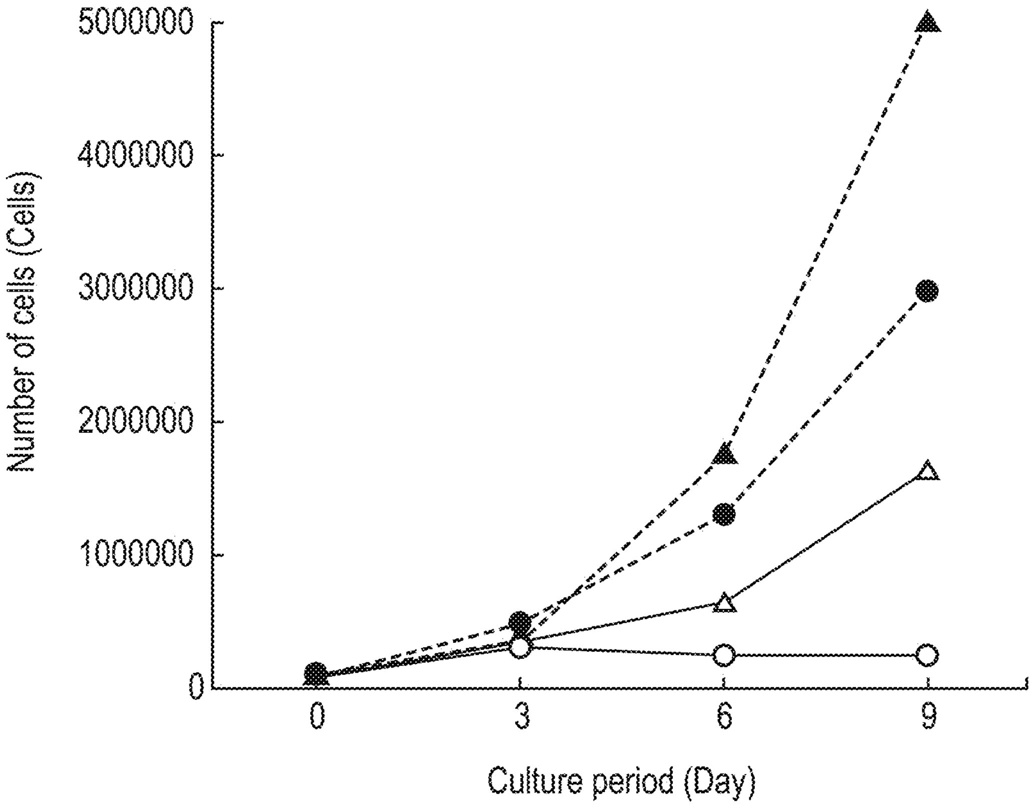
FIG. 8 is a graph illustrating experimental results of Example 2, more specifically temporal changes in the number of cells of PDX-AML-1 isolated from a patient with myeloid leukemia, after introduced with lipid particles having composition B or C and encapsulating siNT or siRUNX1.

FIG. 8 illustrates temporal changes in the number of cells of PDX-AML-1 isolated from a patient with myeloid leukemia, after introduced with lipid particles having composition B or C and encapsulating siNT or siRUNX1. In FIG. 8, the ordinate plots the number of cells (Cells), the abscissa plots the culture period (Days), triangle plots indicate temporal changes in the number of cells having introduced therein the lipid particle with composition B; circle plots indicate temporal changes in the number of cells having introduced therein the lipid particle with composition C; broken line indicates that the encapsulated siRNA is siNT; and the solid line indicates that the encapsulated siRNA is siRUNX1.

Figure 9:
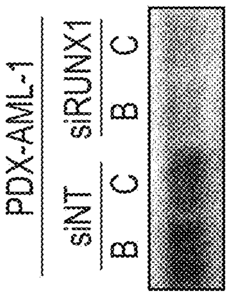
FIG. 9 is a photograph illustrating experimental results of Example 2, more specifically analytical results of RUNX1-expressing protein, from among proteins extracted from PDX-AML-1, which is a cell isolated from a patient with myeloid leukemia, after introduced with lipid particles that encapsulate siNT or siRUNX1.

FIG. 9 illustrates analytical results of RUNX1-expressing protein, from among proteins extracted from PDX-AML-1, which is a cell isolated from a patient with myeloid leukemia, after introduced with the lipid particles that encapsulate siNT or siRUNX1.

Referring to FIG. 8, cell proliferation was found to be more largely suppressed when the lipid particles with composition B or C and encapsulating siRUNX1 were introduced, as compared with the case where the lipid particles with composition B or C and encapsulating siNT were introduced. Referring to FIG. 9, introduction of the lipid particles with composition B or C and encapsulating siRUNX1 was proved to reduce the abundance of RUNX1-expressing protein, and to suppress expression of RUNX1.

Hence, the lipid particles with lipid composition B or C and encapsulating siRUNX1 were proved to demonstrate the suppressive effect on proliferation of myeloid tumor cell and expression of RUNX1, even if the myeloid tumor cell were derived from patient.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for delivering a substance to a myeloid tumor cell, the method comprising:

preparing a substance delivery carrier which comprises a lipid particle and the substance encapsulated in the lipid particle; and contacting the substance delivery carrier with the myeloid tumor cell;

wherein the lipid particle contains a first lipid represented by formula (I):

(I)

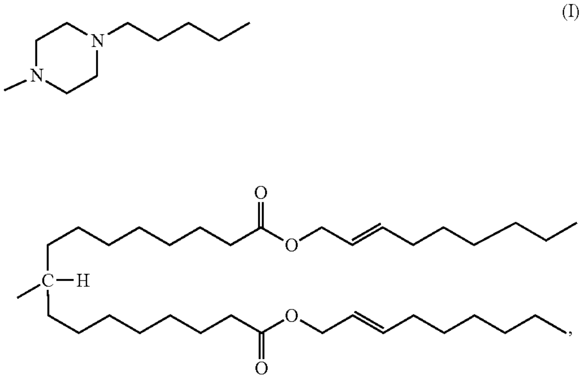

and at least one of cationic lipid, neutral lipid, anti-aggregation lipid, and cholesterol, wherein a mole ratio of the first lipid in a lipid composition of the lipid particle is from 10% to 50%, and the lipid particle exhibits 8.4 pKa or smaller, in an environment with an ionic strength of $3.599 \times 10^{-3}$ mol/dm$^3$.

2. The method of claim 1, wherein the substance contains siRNA that suppresses expression of a gene relevant to onset and progression of the myeloid tumor cell.

3. The method of claim 2, wherein the siRNA contains a sequence complementary to a part of the gene.

4. The method of claim 2, wherein the gene is at least one selected from the group consisting of transcription factor, fusion gene, epigenome control factor, phosphorylating enzyme-related gene, immunosuppressive factor, a ubiquitin-related factor, apoptosis control factor, and non-coding RNA.

5. The method of claim 2, wherein the gene is at least one selected from RUNX1, RUNX2, MECOM, MYB, MYC, HOXA9, MEIS1, HHEX, and ERG.

6. The method of claim 1, wherein the lipid particle further encapsulates at least either a pH adjustor or an osmoregulator.

7. The method of claim 1, wherein the myeloid tumor cell exists in vivo in a subject, and contacting is carried out by administering a composition that contains the substance delivery carrier to the subject.

8. A substance delivery carrier for delivering a substance to a myeloid tumor cell, the substance delivery carrier comprising:

a lipid particle; and the substance encapsulated in the lipid particle, the lipid particle containing at least a first lipid represented by formula (I):

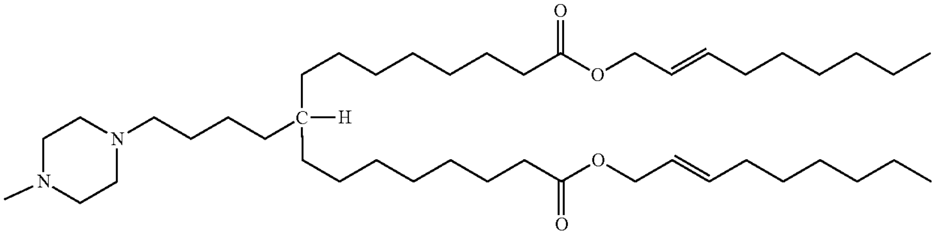

(I)

and at least one of cationic lipid, neutral lipid, anti-aggregation lipid, and cholesterol wherein a mole ratio of the first lipid in a lipid composition of the lipid particle is from 10% to 50%, and the lipid particle exhibits 8.4 pKa or smaller, in an environment with an ionic strength of 3.599×10−3 mol/dm3.

9. The substance delivery carrier of claim 8, wherein the lipid particle is weakly cationic.

10. The substance delivery carrier of claim 8, wherein the substance contains siRNA that suppresses expression of a gene relevant to onset and progression of the myeloid tumor cell.

11. The substance delivery carrier of claim 10, wherein the siRNA contains a sequence complementary to a part of the gene.

12. The substance delivery carrier of claim 10, wherein the gene is at least one selected from the group consisting of transcription factor, fusion gene, epigenome control factor, phosphorylating enzyme-related gene, immunosuppressive factor, a ubiquitin-related factor, apoptosis control factor, and non-coding RNA.

13. The substance delivery carrier of claim 10, wherein the gene is at least one selected from RUNX1, RUNX2, MECOM, MYB, MYC, HOXA9, MEIS1, HHEX, and ERG.

14. The substance delivery carrier of claim 8, wherein the lipid particle further encapsulates at least either pH adjustor or an osmoregulator.

15. A composition comprising the substance delivery carrier of claim 8, and further comprising at least either a carrier or a storage protectant.

16. The composition of claim 15, wherein the storage protectant is present and is dimethylsulfoxide.

* * * * *